(12) United States Patent
De Ketelaere et al.

(10) Patent No.: US 10,206,375 B2
(45) Date of Patent: Feb. 19, 2019

(54) METHOD AND APPARATUS FOR EXAMINING EGGS

(71) Applicant: MOBA GROUP B.V., Barneveld (NL)

(72) Inventors: Bart De Ketelaere, Leuven (BE); Josse De Baerdemaeker, Leuven (BE); Jeroen Evert Jan Brunnenkreef, Enter (NL)

(73) Assignee: MOBA GROUP B.V., Barneveld (NL)

(*) Notice: Subject to any disclaimer, the term of this patent is extended or adjusted under 35 U.S.C. 154(b) by 414 days.

(21) Appl. No.: 14/936,354

(22) Filed: Nov. 9, 2015

(65) Prior Publication Data

US 2016/0057976 A1  Mar. 3, 2016

Related U.S. Application Data

(63) Continuation of application No. 13/883,320, filed as application No. PCT/NL2011/050750 on Nov. 3, 2011, now abandoned.

(30) Foreign Application Priority Data

Nov. 5, 2010 (EP) .................................. 10014328

(51) Int. Cl.
  *G01N 3/48* (2006.01)
  *A01K 43/00* (2006.01)
  (Continued)

(52) U.S. Cl.
  CPC ............... *A01K 43/00* (2013.01); *G01N 3/40* (2013.01); *G01N 3/48* (2013.01); *G01N 29/045* (2013.01); *G01N 33/08* (2013.01)

(58) Field of Classification Search
  CPC ...... A01K 43/00; G01N 33/08; G01N 29/045; G01N 2291/265; G01N 3/40; G01N 3/405
  See application file for complete search history.

(56) References Cited

U.S. PATENT DOCUMENTS 5,728,939 A    3/1998 Moayeri
6,354,148 B2 *  3/2002 Sato .................... G01N 3/52
                                               73/79
(Continued)

FOREIGN PATENT DOCUMENTS

CN    101672827    3/2010
EP    0 738 888     4/1996
(Continued)

OTHER PUBLICATIONS

English Translation of Japanese Notice of Opposition and Notification, Opposition No. 2016-00527.
(Continued)

*Primary Examiner* — Freddie Kirkland, III
(74) *Attorney, Agent, or Firm* — Marvin Petry; Stites & Harbison PLLC

(57) ABSTRACT

This invention relates to a method and apparatus for examining eggs, in particular for determining eggshell characteristics of eggs, the method comprising,
  positioning the eggs to be examined,
  with a deformer, deforming a part of such an egg at least once,
  at least determining deformation contact time, and
  determining the shell stiffness and/or the eggshell strength of such an egg.
Such a manner of detection can be suitably applied to sorting machines for eggs.
With this methodology, in a short time, for a very large number of products, such as eggs in the present case, a quality parameter such as the strength and/or stiffness can be determined.
With such determinations, in an advantageous manner, high requirements set in many fields of technology and industry can be met.

15 Claims, 1 Drawing Sheet

Figure 1:
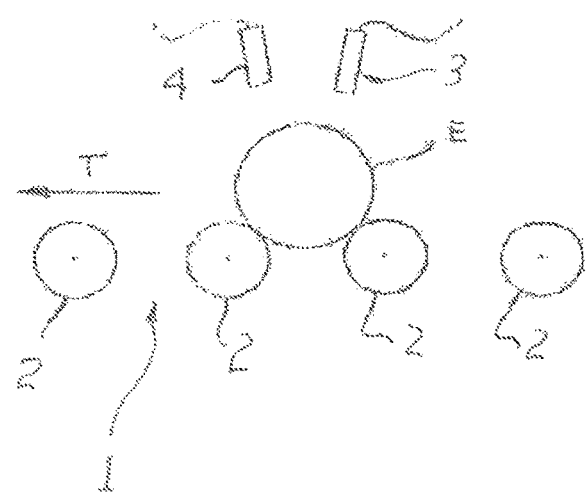

(51) Int. Cl.
*G01N 3/40* (2006.01)
*G01N 29/04* (2006.01)
*G01N 33/08* (2006.01)

(56) References Cited

U.S. PATENT DOCUMENTS

| | | | | |
|---|---|---|---|---|
| 7,284,414 | B2* | 10/2007 | Wu | G01N 3/52 |
| | | | | 73/79 |
| 8,818,746 | B1* | 8/2014 | Johnson | G01N 29/045 |
| | | | | 702/190 |
| 2001/0010170 | A1* | 8/2001 | Sato | G01N 3/52 |
| | | | | 73/79 |
| 2003/0201209 | A1* | 10/2003 | De Baerdemaeker | |
| | | | | G01N 3/405 |
| | | | | 209/576 |
| 2013/0283894 | A1* | 10/2013 | De Ketelaere | A01K 43/00 |
| | | | | 73/78 |

FOREIGN PATENT DOCUMENTS

| | | |
|---|---|---|
| JP | 9-21793 | 1/1997 |
| JP | 2002-030643 | 1/2002 |
| JP | 2004-150946 | 5/2004 |
| JP | 3132446 | 5/2007 |
| WO | WO 01/09602 | 2/2001 |

OTHER PUBLICATIONS

English Translation of Decision of Japanese Appeal Examiner in Japanese Opposition No. 2016-00527.
Notice of Opposition, Opposition No. 2016-700527, now U.S. Pat. No. 5,830,105, dated Jun. 8, 2016, 37 pages.
Notification sent in respect to Opposition, Opposition No. 2016-700527, now U.S. Pat. No. 5,830,105, dated Jul. 19, 2016, 2 pages.

* cited by examiner

METHOD AND APPARATUS FOR EXAMINING EGGS

This application is a continuation of U.S. patent application Ser. No. 13/883,320, filed Jul. 15, 2013, which is a 371 application of PCT/NL2011/050750, filed Nov. 3, 2011, both incorporated herein by reference.

The present invention relates to a method and apparatus for examining eggs. The present invention relates in particular to a method and apparatus for determining eggshell characteristics of eggs.

Methods and apparatuses for determining eggshell characteristics of eggs are generally known. In the following, a few often applied examples thereof will be described in further detail.

In EP738888, to be considered incorporated herein in its entirety by reference, a detector for determining cracks in eggshells is described. With this detector, the sound signal produced by a small ball briefly bouncing on a surface area of an egg is measured. More particularly, the curve of the sound intensity oscillating over time of the bouncing of the ball provides information about whether or not this surface area is intact. By carrying out this determination several times for the same egg, the condition of a shell of an egg, i.e. the presence or absence of cracks or ruptures in the eggshell, is mapped in an automated manner whereby a value for this condition is generated. Such a value is used as a criterion in the sorting of eggs.

In NL1018940, a method and apparatus are discussed wherein the vibrational properties of eggs in combination with, inter alia, mass determinations allow the determination of quality parameters of eggs. Here, in particular, use is made of the manner of analysing such vibrations as described in U.S. Pat. No. 5,696,325 and in "Assessment of some physical quality parameters of eggs based on vibration analysis", Peter Coucke, thesis Leuven, March 1998.

In the past, as described in Coucke, a reliable criterion for determining the quality of eggs has been sought. For instance, in packing stations for eggs, in particular the shell stiffness is considered a quality parameter. To that end, for each batch of eggs, at random, with the help of a test bank, under semi-static compression, the shell stiffness or spring constant of the eggshell of a number of eggs is determined. In this context, mention is also made of eggshell strength. Such a random test follows a protocol prescribing for such an egg how to position it, how to compress it, and how to measure the compression. A more detailed description of this methodology is described in, for instance, M. M. Bain "Recent advances in the assessment of eggshell quality and their future application", XXII World Poultry Congress, Istanbul, Jun. 8-13, 2004. The above-mentioned methodology can be carried out destructively as well as non-destructively. It will be clear to the skilled person that such a method is not suited for large scale application of industrial sorting where per hour, for instance, 180,000 eggs must be tested.

In order to provide this shell stiffness (and/or the eggshell strength) also during processing and sorting that involve the above-mentioned numbers, the method according to the present invention comprises:

positioning the eggs to be examined, with a deformer, deforming a part of such an egg at least once, at least determining deformation contact time, and determining the shell stiffness and/or eggshell strength of such an egg, in particular utilizing the deformation contact time determined for this egg. In an advantageous manner, and with existing equipment, in a rapid and efficient manner, an important quality parameter can be determined for large batches of eggs.

In particular, it appears that the deformation contact time is inversely proportional to the shell stiffness (and the eggshell strength). The shorter the deformation contact time, the better (higher) the shell stiffness and the higher the eggshell strength. By determining the deformation contact time, thus, relatively simply, an estimate can be provided of the eggshell stiffness (and shell strength).

The deformation contact time mentioned is also called the impact duration or the finite deformation contact time, i.e. the time duration during which the two impacting elements (i.e. the egg and the deformer) are in direct mechanical contact (touch each other).

With this methodology, in a relatively short time, for a large amount of products, as in the present case, for instance, for eggs, a quality parameter such as the strength and/or stiffness can be determined.

With such determinations, in an advantageous manner, high requirements set in many fields of technology and industry can be met.

Such a method of detection can be suitably applied to sorting machines for eggs.

The method comprises, for instance, determining, during deforming (of a part of the egg), the deformation contact time.

It is noted that determination of elastic properties of objects under deformation is known according to an approach called the Hertz model. This model is based on a publication of Heinrich Hertz, "Über die Berührung fester elastischer Körper", Journal für reine und angewandte Mathematik 92, 156-171 (1881). As a basis for a lot of research into properties of materials, it has been used in developing many methodologies and types of detectors. An example thereof is described in U.S. Pat. No. 3,106,837. Depending on the signals measured upon oscillating load, more particularly the resonance frequencies of the objects subjected to this load, deviations in mechanical properties such as elasticity modulus, hardness, and geometry can be established.

In further elaborations, the method according to the invention has one or more of the characteristics:

that further, the initial contact velocity of the deformer is determined;

that further, (for a specific egg) the deflection or deformation from an initial position is measured; and/or:

that the deformation is carried out while bouncing, for instance by having the deformer bounce against the egg.

A deformer initial contact velocity is preferably used together with the deformation contact time mentioned for determining the eggshell stiffness (and/or eggshell strength), which appears to lead to particularly good results.

The present invention further provides an apparatus for examining eggs, in particular for determining eggshell characteristics of eggs, the apparatus comprising:

a deformer for at least once deforming a part of such an egg, a detector for determining at least deformation contact time, for instance during deforming, and a central processing unit for determining with this deformation contact time the shell stiffness and/or the eggshell strength of such an egg.

With such an apparatus, simply and rapidly, a highly reliable value for the shell stiffness and/or the eggshell strength of an egg can be determined.

In further elaborations of the invention, the apparatus has one or more of the following characteristics:

that the deformer comprises a ball bouncing/to be bounced on the egg;

that the apparatus is designed for determining, for instance measuring, an initial contact velocity of the deformer, for instance as derivative of a bouncing time, equal to the time duration between two successive impacts;

that the bouncing of the ball is controlled by substantially the field of gravity;

that the bouncing of the ball is controlled by substantially an electromagnetic field;

that the bouncing of the ball is controlled by a combination of an electromagnetic field and the field of gravity;

that further, the initial contact velocity is determined during the mentioned bouncing time;

that the apparatus further comprises an optical detector for determining, for such an egg, the deflection or deformation from an initial position; and/or that the optical detector comprises a camera or a laser vibrometer.

The apparatus can be configured, for instance, to use a deformer initial contact velocity (together with the deformation contact time) in determining the shell stiffness and/or the eggshell strength.

In a further use of the method and/or the apparatus according to the present invention, this method or this apparatus can be directly used and applied in sorting eggs. For instance in EP738888, it is described how such detection can be carried out during transport of eggs over, for instance, a roller conveyor. Such a roller conveyor is a main element of sorting machines known to any skilled person, mostly as part of a sorting system.

Figure 2:
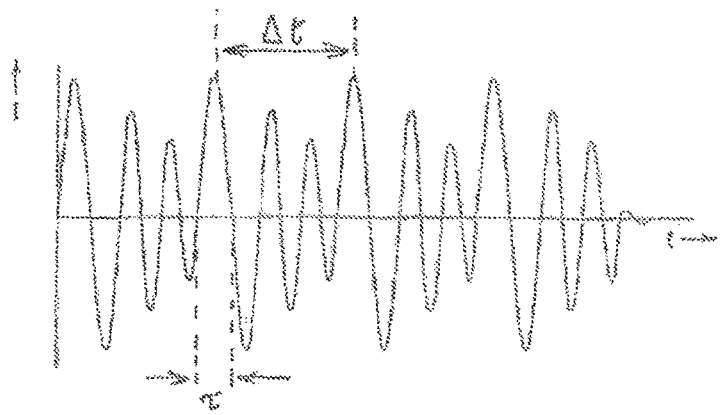

In the following, further details will be given and explained in further detail on the basis of a drawing, in which FIG. 1 schematically shows an example of an apparatus according to the invention, and FIG. 2 shows an example of a detection signal for determining the shell stiffness (and/or shell strength) of an egg.

FIG. 1 gives a schematic view of a roller conveyor 1 as is generally known and used in sorting machines for eggs. An egg E rests on rollers 2, the rollers 2 forming at least one row, these rollers 2 being usually provided on axles (in this schematic drawing perpendicular to the plane of the drawing), and these rollers being usually mutually connected at the ends of the axles by endless chains that are guided over end wheels and are driven at one of the ends. It will be clear to the skilled person that use of such rollers 2 enables an accurate and repeatable positioning of products such as eggs. In this FIGURE, the conveying direction is indicated with T. Further, there is the possibility of arranging for rotation of the rollers with axles so that the eggs themselves rotate or spin. Such a rotating movement enables detection operations over the entire egg surface.

Further, in FIG. 1, an excitation member or deformer 3 and an optical detector 4 are indicated. Such an excitation member or deformer is known in this field of technology and described in, for instance, EP738888 mentioned hereinabove, and in EP1198708 and in EP1238582. In contrast with what was customary hitherto, with this apparatus, contact times upon tapping or impacting can be determined. More particularly, a hammer as mentioned in EP1238582 can be provided with an accelerometer, for instance a piezo element, for measuring such a contact time. Such accelerometers can be of the type that energizes the inflation of air bags in automobiles upon collision. In the following, the use of the detector according to EP738888 will be described in further detail on the basis of FIG. 2.

The optical detector 4 can be a camera for taking rapid shots, or also a laser vibrometer or measuring optics generally known. Such optical equipment allows determination of times, distances and velocities over very short time durations and is therefore highly suitable for carrying out such detection in the above mentioned sorting machines.

In FIG. 2, a signal is represented that is produced by the detector as is extensively described in EP738888. This signal shape shows how a ball bounces on an egg several times. More particularly, there is shown the interval of time of the sound intensity I that is measured by a microphone in the column of which the bouncing ball forms the end. Four collisions between the ball and the egg can be seen and hence also four bouncing movements. The shape of the signal for one single bouncing movement is the result of the standing wave in the air column between the ball and the microphone, and is damped.

More particularly, in FIG. 2 a time duration τ is indicated. This time duration is measured between two successive zero axis crossings of the first maximum intensity to be recognized for each bounce, and is substantially equal to the earlier mentioned contact time between the ball and an egg. Deviations thereof should be attributed to the construction of the detector, i.e. the distances to the microphone and the characteristics of the microphone. If required, this can be corrected for.

Further indicated is the time duration of such a single reciprocating movement, also to be called bounce time Δt. This time duration makes it possible, with the control that is applied to the ball, i.e. in the field of gravity in combination with an electromagnetic field, to determine the velocity ($V_{n0}$) of the ball at the time of impact, the initial contact velocity. For the ball bouncing on the egg, for instance, the following estimate can be derived for the initial contact velocity $V_{n0}$:

$$v_{n0}=K1 \cdot \Delta t - K2 \quad (1)$$

wherein Δt is the bouncing time(s) and K1 and K2 are empirically determinable constants.

The initial contact velocity can also be determined in another manner (for instance by processing optical measuring data), which will be clear to the skilled person. As follows further from patent publication EP738888A1 incorporated herein by reference, the apparatus can be configured, for instance, for carrying out/controlling the bouncing such that a predetermined initial contact velocity ($v_c$) is achieved.

With the optical detectors mentioned, deflection or deformation from an initial position can be measured.

The above-mentioned determinations make it possible to determine a shell stiffness parameter which parameter is derived with the Hertz model for such an egg-ball system. It is known to any skilled person how such a parameter relates to the above-mentioned shell stiffness or eggshell strength as determined according to the above-mentioned compression methodology, or also a specific stiffness determined in another way.

It has appeared that for such an egg-ball system a highly effective shell stiffness parameter determination can already be carried out with the contact time alone. When a greater precision is required, the initial contact velocity ($v_{n0}$) can be added in determining the shell stiffness parameter.

Thus, it appears that the following relation can be used for determining the stiffness $K_H$, also called Hertz stiffness:

$$K_H = \left(\frac{C}{\tau}\right)^{5/2} V_{n0}^{-1/2} m \qquad (2)$$

wherein $K_H$ is the Hertz stiffness (N/m$^{3/2}$), c is a constant (c=3.2145), $v_{n0}$ is the initial contact velocity (m/s), $\tau$ is the deformation contact time(s) and m is the effective mass of the system, (kg), i.e.:

$$m = \frac{m_1 + m_2}{m_1 + m_2} \qquad (3)$$

wherein $m_1$ is the mass of the deformer (in this case the bouncing ball) and $m_2$ is the mass of the respective egg.

It will be clear to the skilled person that variants of the above-mentioned procedure are possible whereby, for instance, another combination of magnetic fields and electric fields is utilized. Further, the accelerometer will provide a different type of determination and calculation.

Furthermore, apparatuses can be used where tapping is carried out not with a ball but with a pin or a needle. There too, in a manner similar to that indicated hereinabove, it is possible with the Hertz-model mentioned to derive the relation with which the shell stiffness can be determined. Further, unexpected deviations therefrom can provide an indication of, for instance, a defect or a contamination.

Although the invention is directed to measuring the physical characteristic of eggs, a simple modification of such an apparatus can provide similar determinations on other products or articles. To be considered here are metal products such as bearings, and ceramic products, or also glass, or fruit products or food products suitable for such deformations, but the examples are not limited to these. It will therefore be clear that other variants are considered to fall within the scope of protection of the appended claims.

The invention claimed is:

1. A method for examining eggs, in particular for determining eggshell characteristics of eggs, the method comprising,
   positioning the eggs to be examined,
   with a deformer, deforming a part of such an egg such that the deformer is in actual contact with the egg for a finite deformation contact time,
   determining deformation contact time, and
   determining shell stiffness and/or eggshell strength of such an egg, by utilizing as at least one factor the determined finite deformation contact time.

2. A method according to claim 1, including determining a deformer initial contact velocity.

3. A method according to claim 1, including measuring the deformation from an initial position.

4. A method according to claim 1, wherein the deformation step is carried out while bouncing, the deformer against the egg.

5. A method for sorting eggs wherein the method according to claim 1 is used for determining, during sorting, the eggshell stiffness and/or the eggshell strength.

6. An apparatus for examining eggs, in particular for determining eggshell characteristics of eggs, the apparatus comprising
   a deformer arranged to deform a part of such an egg such that the deformer is in actual contact with the egg for a finite deformation contact time,
   a detector arranged to determine the finite deformation contact time, and
   a central processing unit arranged to determine, using as at least one factor, the finite deformation contact time, shell stiffness and/or eggshell strength of such an egg.

7. An apparatus according to claim 6, wherein the deformer comprises a ball to be bounced on the egg, the apparatus optionally being configured for measuring an initial contact velocity of the ball as a derivative of a bouncing time, equal to the time duration between two successive impacts.

8. An apparatus according to claim 7, wherein the ball is arranged in the apparatus such that the bouncing of the ball is controlled substantially by gravity.

9. An apparatus according to claim 7, wherein the ball is arranged in the apparatus such that the bouncing of the ball is controlled substantially by an electromagnetic field.

10. An apparatus according to claim 7, wherein the ball is arranged in the apparatus such that the bouncing of the ball is controlled by a combination of an electromagnetic field and of gravity.

11. An apparatus according to claim 7, wherein the apparatus further comprises an optical detector which determines for such an egg the deformation from an initial position.

12. An apparatus according to claim 11, wherein the optical detector comprises a camera or a laser vibrometer.

13. An apparatus according to claim 6, wherein the apparatus is configured to determine an initial contact velocity of the deformer.

14. An apparatus according to claim 6, wherein the deformer is configured in use to have an initial contact velocity which together with the finite deformation contact time determines shell stiffness and/or the eggshell strength.

15. An apparatus for sorting eggs according to claim 6 which is arranged to determine during this sorting, the eggshell stiffness and/or the eggshell strength.

* * * * *